United States Patent

Ockuly et al.

[11] Patent Number: 5,833,673
[45] Date of Patent: Nov. 10, 1998

[54] GUIDING INTRODUCER SYSTEM FOR USE IN THE TREATMENT OF LEFT VENTRICULAR TACHYCARDIA

[75] Inventors: John D. Ockuly, Minnetonka; James A. Hassett, Bloomington, both of Minn.

[73] Assignee: Daig Corporation, Minnetonka, Minn.

[21] Appl. No.: 422,702

[22] Filed: Apr. 14, 1995

Related U.S. Application Data

[63] Continuation-in-part of Ser. No. 389,252, Feb. 16, 1995, Pat. No. 5,722,400, and a continuation-in-part of Ser. No. 333,579, Nov. 3, 1994, Pat. No. 5,628,316.

[51] Int. Cl.$^6$ ................................................. A61M 25/00
[52] U.S. Cl. ........................... 604/281; 600/585; 606/41; 607/122
[58] Field of Search ....................... 600/314, 585; 606/41; 607/122; 604/280, 281

[56] References Cited

U.S. PATENT DOCUMENTS

| | | |
|---|---|---|
| 4,033,331 | 7/1977 | Guss et al. . |
| 4,117,836 | 10/1978 | Erikson . |
| 4,581,017 | 4/1986 | Sahsta . |
| 4,641,649 | 2/1987 | Walinsky et al. . |
| 4,810,244 | 3/1989 | Allen . |
| 4,882,777 | 11/1989 | Narula . |
| 4,883,058 | 11/1989 | Ruiz . |
| 4,898,591 | 2/1990 | Jang et al. . |
| 4,935,017 | 6/1990 | Sylvanowicz . |
| 4,945,912 | 8/1990 | Langberg . |
| 5,016,640 | 5/1991 | Ruiz . |
| 5,120,323 | 6/1992 | Shockey et al. . |
| 5,172,699 | 12/1992 | Svenson et al. . |
| 5,215,540 | 6/1993 | Anderhub . |
| 5,222,501 | 6/1993 | Idekar et al. . |
| 5,231,994 | 8/1993 | Harmjanz . |
| 5,242,441 | 9/1993 | Avitall . |
| 5,267,982 | 12/1993 | Sylvanowicz . |
| 5,279,546 | 1/1994 | Mische et al. . |
| 5,290,229 | 3/1994 | Paskar . |
| 5,304,131 | 4/1994 | Paskar . |
| 5,628,316 | 5/1997 | Swartz et al. ........................... 600/374 |

FOREIGN PATENT DOCUMENTS

| | | |
|---|---|---|
| 0277366 | 8/1988 | European Pat. Off. . |
| 0656217 | 6/1995 | European Pat. Off. . |
| 0670168 | 9/1995 | European Pat. Off. . |
| 9212754 | 8/1992 | WIPO . |
| 19307 | 11/1992 | WIPO . |

OTHER PUBLICATIONS

Singer, I. et al. "Catheter Ablation for Arrhythmias," Clinical Manual of Electrophysiology, pp. 421–431 (1993).
Falk, R.H. et al. "Atrial Fibrillation Mechanisms and Management," pp. 359–374 (1992).
Horowitz, L.N. "Current Management of Arrhythmias" pp. 373–378 (1991).
Gallagher, J.J. et al. "Catheter Technique for Closed Chest Ablation of the Atrioventricular Conduction System, " N. Engl. J. Med., vol. 306, pp. 194–200 (1982).
Tracy, C.M. "Radiofrequency Catheter Ablation of Ectopic Atrial Tachycardia Using Paced Activation Sequence Mapping," J. Am. Coll. Cardiol. vol. 21, pp. 910–917 (1993).
Saul, J.P. et al. "Catheter Ablation of Accessory Atrioventicular Pathways in Young Patients: Use of Long Vascular Sheaths, The Trans–septal Approach & a Retrograde Left Posterior Parallel Approach" J. Amer. Coll. Card., vol. 21, No. 3, pp. 571–583 (1993).
Swartz, J.F. et al. Radiofrequency Endocardial Catheter Ablation of Accessory Atrioventricular Pathway Atrial Insertion Sites Circulation, vol. 87, No. 2, pp. 487–499 (1993).

*Primary Examiner*—Lee S. Cohen
*Attorney, Agent, or Firm*—Scott R. Cox

[57] ABSTRACT

A process for the treatment of ventricular tachycardia in the left ventricle using a retrograde approach by use of ablating and/or mapping catheters guided by a guiding introducer system. Also disclosed are predetermined shapes for an inner and outer guiding introducers which comprise the guiding introducer system.

20 Claims, 4 Drawing Sheets

GUIDING INTRODUCER SYSTEM FOR USE IN THE TREATMENT OF LEFT VENTRICULAR TACHYCARDIA

This application is a continuation-in-part of application Ser. No. 08/389,252 filed Feb. 16, 1995 now U.S. Pat. No. 5,722,400, and also a continuation-in-part of application Ser. No. 08/333,759, filed Nov. 3, 1994, now U.S. Pat. No. 5,628,316.

BACKGROUND OF INVENTION

1. Field of Invention

This invention relates to introducers. More particularly, this invention relates to a guiding introducer system for use within the left ventricle of the human heart for the treatment of left ventricular tachycardia.

2. Prior Art

Introducers and catheters have been in use for medical procedures for many years. For example, one use has been to convey an electrical stimulus to a selected location within the human body. Another use is to monitor and make measurements for diagnostic tests within the human body. Catheters may be used by a physician to examine, diagnose and treat while positioned at a specific location within the body which is otherwise inaccessible without more invasive procedures. In use, catheters may be inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,215,540, 5,016,640 and 4,883,058 disclose catheters for selective coronary angiography of the right coronary artery. U.S. Pat. No. 5,242,441 discloses a deflectable catheter for ablation procedures in the ventricular chamber. See also U.S. Pat. No. 4,033,331. In addition, U.S. Pat. No. 4,898,591 discloses a catheter with inner and outer layers containing braided portions. The '591 patent also discloses a number of different curvatures for intravascular catheters. Thus, there are a number of references which disclose catheters with predetermined shapes, designed for use during specific medical procedures generally associated with the heart or the vascular system. Because of precise physiology of the heart and the vascular system, catheters or introducers with precisely designed shapes for predetermined uses within the human heart and vascular system are increasingly important.

In addition to single catheter with various curvatures, U.S. Pat. No. 4,581,017 discloses an inner and outer guide catheter, (numbers 138 and 132), for use with a balloon catheter for treatment of coronary arteries. U.S. Pat. No. 5,267,982 discloses a catheter assembly and methods for catheterization of coronary arteries wherein an inner catheter (50) and outer catheter (52) are used in combination for the treatment of right and left coronary angiographic procedures. See also U.S. Pat. No. 4,935,017 which discloses a similar device. U.S. Pat. No. 5,290,229 discloses a straight outer sheath and a preformed inner catheter for use in the heart. See also U.S. Pat. Nos. 5,304,131, 5,120,323, 4,810,244 and 5,279,456.

Catheter ablation of accessory pathways using a long vascular sheath by means of a transseptal or retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *J. Amer. Coll. Card.*, Vol. 21, no. 3, pps 571–583 (Mar. 1, 1993). See also Swartz, J. F. "Radiofrequency Endocardial Catheter Ablation of Accessory Atrioventricular Pathway Atrial Insertion Sites" Circulation, Vol. 87, no. 2, pps. 487–499 (February 1993).

U.S. Pat. No. 4,641,649 discloses the use of high frequency energy for the treatment of tachycardia or cardiac dysrhythmia. See also U.S. Pat. Nos. 5,246,438 and 4,945,912 for the use of radio frequency energy for ablation of cardiac tissue. In addition, various articles have disclosed the ablation of specific locations within the heart by use of energy, in particular, radio frequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, U.S. Pat. No. 5,172,699 discloses a general process for the identification and ablation of ventricular tachycardia sites. See also U.S. Pat. Nos. 5,222,501 and 5,242,441.

In addition, the use of radio frequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation 87:487–499 (1993). See also Tracey, C. N. "Radio Frequency Catheter Ablation of Ectopic Atrial Tachycardia Using Paced Activation Sequence Mapping" J. Am. Coll. Cardiol. 21:910–917 (1993).

Accordingly, it is an object of this invention to prepare a guiding introducer system for selected medical procedures in the left ventricle.

It is a further object of this invention to prepare a guiding introducer system for use in selected electrophysiology procedures within the left ventricle of the heart.

Another object of this invention is to prepare a guiding introducer system for use in selected ablation procedures within the left ventricle of the heart.

It is a still further object of this invention to prepare a guiding introducer system for use in the selected ablation of sites in the left ventricle of the heart for the treatment of left ventricular tachycardia.

These and other objects are obtained by the design of the guiding introducer system disclosed in the instant invention.

SUMMARY OF INVENTION

The instant invention includes a process for the treatment of ventricular tachycardia within the left ventricle of the heart comprising (a) introducing into the left ventricle a guiding introducer system, wherein said guiding introducer system is comprised of an inner and outer guiding introducer, wherein each of the inner and outer guiding introducers contains a lumen running lengthwise therethrough, a proximal and a distal end;

(b) introducing the inner guiding introducer into the lumen of the outer guiding introducer;

(c) introducing into the lumen of the inner guiding introducer an ablating or mapping catheter containing a proximal and distal end, wherein said catheter has one or more electrodes located at or near the distal end of the catheter;

guiding the catheter to a selected location within the left ventricle by use of the guiding introducer system; and mapping and/or ablating the selected location within the left ventricle by use of the electrodes of the catheter.

In addition, the instant invention is a guiding introducer system to be used in the left ventricle for treatment of ventricular tachycardia comprising an inner and an outer guiding introducer. Both the inner and outer guiding introducers contain first and second sections. The inner guiding introducer is longer than the outer guiding introducer so that it may be extended out from the lumen of the outer guiding introducer to form various curves and shapes for the overall guiding introducer system.

DESCRIPTION OF THE INVENTION.

A typical human heart includes a right ventricle, a right atrium, left ventricle and left atrium. The right atrium is in fluid communication with the superior vena cava and the inferior vena cava. The atrioventricular septum separates the atria from the ventricles. The tricuspid valve contained within the atrioventricular septum communicates the right atrium with the right ventricle. The mitral valve contained within the atrioventricular septum communicates the left atrium with the left ventricle. On the inner wall of the right atrium, where it is connected with the left atrium, is a recessed portion, the fossa ovalis. Between the fossa ovalis and the tricuspid valve is the opening or ostium for the coronary sinus. The coronary sinus is a large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with Wolff-Parkinson-White syndrome have an arrhythmia, the cause of which is believed to be the existence of an anomalous conduction pathway or pathways that connect the atrial muscle tissue directly to the ventricular muscle tissue, thus by-passing the normal His-Purkinje system. These pathways are usually located in the fibrous tissue that connect the atrium and the ventricle.

Another arrhythmia is ventricular tachycardia ("VT"). VT is a disease of the heart in which the heart's normal arrhythmic contraction is altered. Frequently, the rate of heart beat is too fast although the conditions of the disease itself are generally quite complex. VT occurs most often in patients following a myocardial infarction. A myocardial infarction, commonly referred to as a heart attack, is a loss of blood to a region of the heart causing the myocardial tissue in that region to die and be replaced by an area of scar tissue known as a myocardial infarct. Frequently, the myocardial infarct is present in the left ventricle.

As a result of the myocardial infarct, circular pathways ("reentry circuits") are frequently created within the left ventricle for the conduction of the electrical impulses of the heart. These reentry circuits cause the electrical impulses of the heart to travel in circles about the myocardial infarct, frequently causing an erratic and sometimes accelerated beating of the heart. These reentry circuits may also occur around discreet elements of the heart, such as valves. In addition, the reentry circuits sometime occur around both the myocardial infarct and the discreet elements of the heart.

In the past VT has been treated by the use of drugs such as lidocaine, quinidine and procainamide. More recently, beta-blocking drugs have been used for its treatment. In cases where drug therapy has been ineffective, surgical procedures have been used to excise the tissue causing the arrhythmia. The treatment involves one of a combination of procedures such as Gerard Guiradon's Full Encircling Endocardial Ventriculotomy (FEEV), Resection (removal of electrically abnormal tissue) and Peeling (shaving off layers of abnormal endocardial tissue, until only healthy tissue is exposed). Obviously such procedures are high risk, frequently requiring prolonged periods of hospitalization and recuperation. As an alternative to these procedures, catheters have been used for the diagnosis and treatment of cardiac arrhythmias including, specifically, VT. See, for example, U.S. Pat. No. 5,222,501.

Individual applications of ablation energy are frequently unsuccessful at breaking up the reentrant circuit, and the energy applications may have to be repeated several times. This may be because the tip is not positioned correctly at the beginning of the energy application or that the catheter tip moves during the attempted ablation. Another problem can be that even though the tip electrode is located correctly, there may not be enough contact pressure between the tissue and the electrode to facilitate sufficient current to flow through the tissue to properly affect said tissue. This is especially true in the very thick ventricular tissue where the offending tissue may be deep within the myocardium or even epicardial. The procedure may be very time consuming. It may require catheter exchanges to replace a defective or inappropriately selected catheter. Advancing the catheter through the vasculature to the aortic arch into the LV and mapping to find the appropriate location is very difficult with the unaided catheter. To effectively ablate the ventricular tissue, the ablation catheter must be positioned precisely within the ventricle and maintained in contact with the ventricular tissue throughout the energy application. Such procedures may require the ablation electrode of the ablation catheter to remain in contact with the ventricular tissue for an extended period of time, well over a minute. This is particularly difficult when the heart is beating, sometimes irregularly, during the entire ablation procedure. Thus, it is critical that the ablation electrode be maintained at the desired location and also be constrained from movement relative to the tissue being ablated throughout the energy application.

Currently the most common approach to the positioning of an ablation catheter in the left ventricle for ablation procedures is to introduce the catheter into the femoral artery using a standard introducer and advance it toward and through the aorta, across the aortic valve into the left ventricle and then position the electrode of the catheter adjacent to the wall of the left ventricle which is near the reentry circuits. This is commonly referred to as the "retrograde" approach. Specific locations are chosen for the mapping or ablation of the ventricular tissue, including specifically locations on the lateral freewall, posterior freewall, septal wall and anterior freewall.

Mere introduction of the ablation and mapping catheter into the left ventricle for a retrograde approach is not sufficient to effectively and efficiently perform the ablation procedures on the reentry circuits. The medical practitioner commonly monitors the introduction of the catheter and its progress through the vascular system by a fluoroscope. Such fluoroscopes can not easily identify the specific features of the heart in general, and the critically important structures of the left ventricle in specific, thus making placement of the ablation electrode difficult. This placement is especially difficult as the beating heart is in motion. In addition, the catheter will be moving within the left ventricle as blood is being pumped through the heart throughout the procedure. Also, the aortic valve continues to open and close placing additional strain and pressures on the catheter. Further, because of the difficulty of properly locating the catheter, extended exposure to fluoroscopy may be inevitable. However, such excessive exposure is certainly undesirable.

The guiding introducer system of the instant invention addresses and solves these problems. Referring now to FIGS. 2A, 2B, 3A and 3B, the guiding introducer system of the present invention for use in the left ventricle for the treatment of VT is comprised of an inner and an outer guiding introducer. The inner guiding introducer is preferably longer than the outer guiding introducer so that its distal end may be extended out from the distal end of the outer guiding introducer to form various curves and shapes. In use, the inner guiding introducer is inserted into the outer guiding introducer until the distal end of the inner guiding introducer extends out from the distal end of the outer guiding introducer. The inner and outer guiding introducers are generally each comprised of two sections. (Each section is preferably formed as an integral portion of the entire guiding introducer without discrete divisions. However, the division of each of the guiding introducers into two different sections for discussion better illustrates the overall shape of the guiding introducers.) Each of the guiding introducers will be shown in two views. In each of the views for ease of analysis, the inner and outer guiding introducer will be secured to a valve for attachment to a conventional side port tubing and stop cock. In each such arrangement, the shape of the inner or outer guiding introducer and each of its sections will be described, making reference to its position in relation to the side port and side port tubing, where the proximal end of the inner and outer guiding introducer is secured to the side port tubing. In the first referenced figure (FIGS. 2A and 3A), the side port tubing is generally viewed as if it is behind the first section of the inner or outer guiding introducer. The remaining figures (FIGS. 2B and 3B) will show the inner or outer guiding catheter after clockwise rotation about the axis of the first section of the inner or outer guiding introducer when viewed from the perspective of the proximal end of the respective guiding introducers.

The first section of the inner guiding introducers is a conventional, elongated, hollow, generally straight section of sufficient length for introduction into the patient and for manipulation from the point of insertion to the specific desired location within the heart. (The overall length of the first section as shown in the figures has been reduced for ease of viewing.)

Figure 2A:
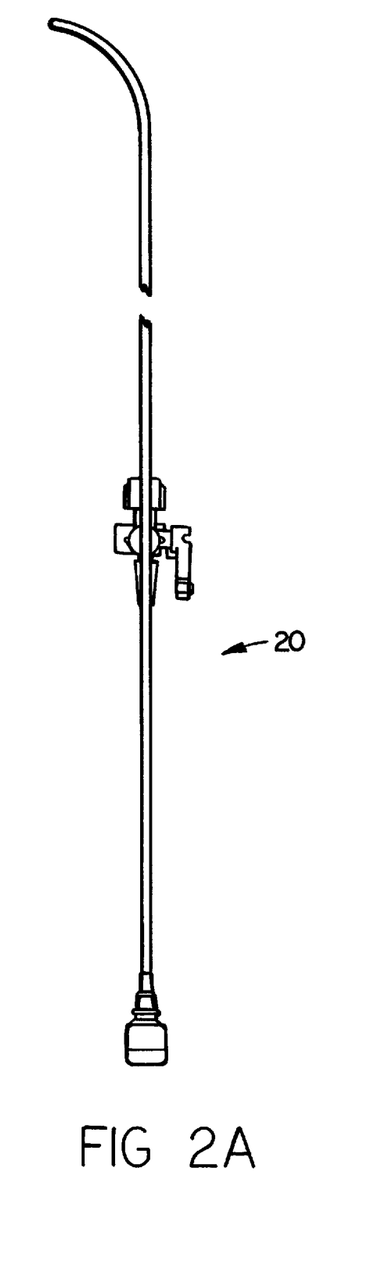
FIG. 2A is a side view of the inner guiding introducer for use in the treatment of ventricular tachycardia in the left ventricle, wherein the side port tubing attached to the proximal end of the inner guiding introducer is located directly behind the first section of the inner guiding introducer.
Figure 2B:
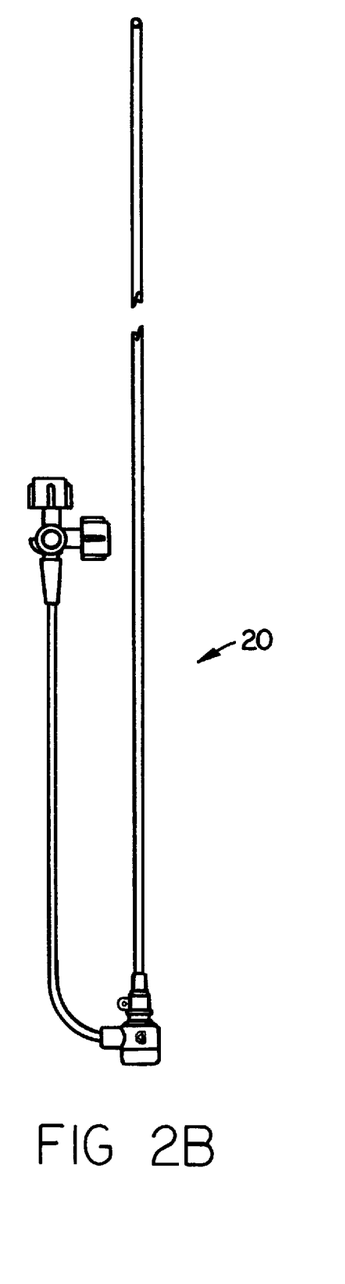
FIG. 2B is a side view of the inner guiding introducer rotated 90° clockwise from the position of FIG. 2A, when viewed from the perspective of the proximal end of the inner guiding introducer, such that the side port is directed to the left of the inner guiding introducer.

Merged with the distal end of the first section of the inner guiding introducer is the second section which is a smooth, generally flat curve, curving to the left as shown in FIG. 2A. The curve of FIG. 2A has a radius of from about 0.5 in. to about 1.5 in. and preferably from about 0.7 in. to about 1.3 in. The extent of the arc of the curve is from about 45 to about 135 degrees and preferably from about 60 to about 120 degrees of arc, ending in the distal tip of the inner guiding introducer. Although this second section is preferably a single curve, alternatively two or more separate curved sections each with the same or different curvatures and radii can be used alone or in combination with one or more straight sections as long as the combination of separate curves and straight sections creates generally the same overall curvature of this second section of about 45 to about 135 degrees, and preferably from about 60 to about 120 degrees. The first and second sections are preferably coplanar (within about 15 degrees of coplanar).

Figure 3A:
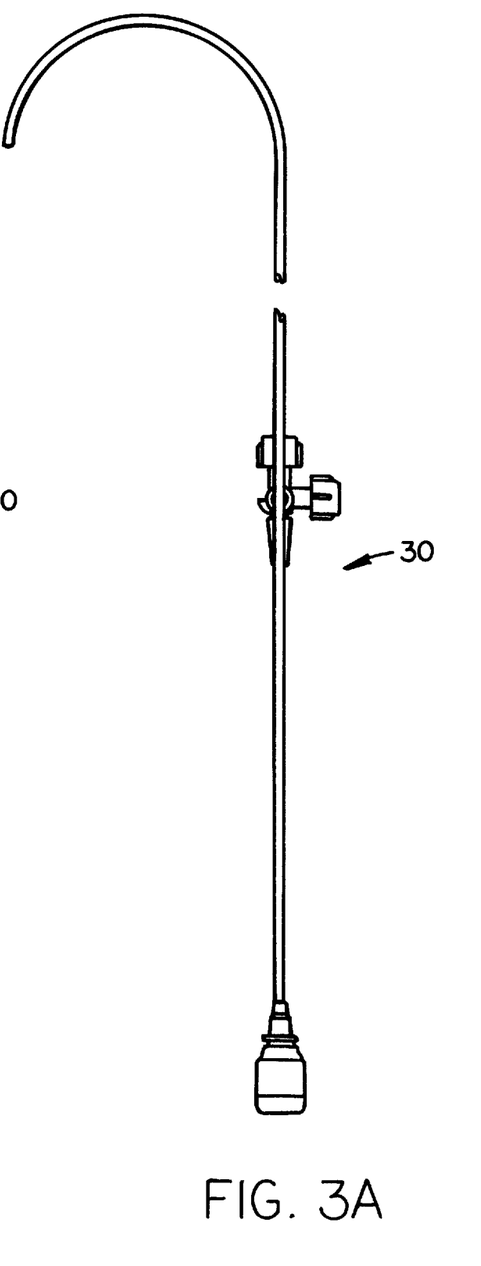
FIG. 3A is a side view of the outer guiding introducer for use in the treatment of ventricular tachycardia in the left ventricle, wherein the side port tubing attached to the proximal end of the outer guiding introducer is located directly behind the first section of the outer guiding introducer.
Figure 3B:
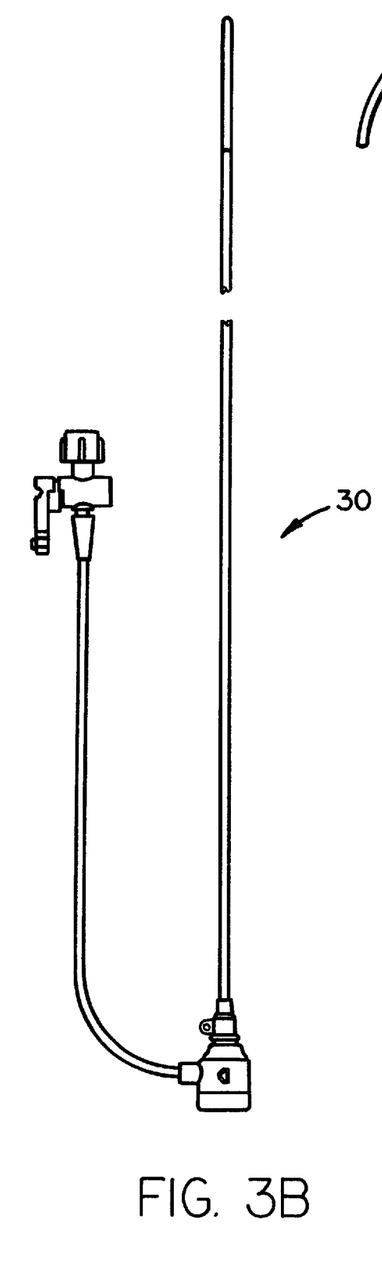
FIG. 3B is a side view of the outer guiding introducer rotated 90° clockwise from the position of FIG. 3A, when viewed from the perspective of the proximal end of the outer guiding introducer, such that the side port is directed to the left of the outer guiding introducer.

The outer guiding introducer (FIGS. 3A and 3B) is designed for use with the inner guiding introducer in the treatment of left ventricular tachycardia in the left ventricle. The outer guiding introducer is also divided into two separate sections. The first section is a conventional, generally elongated, hollow, straight section of sufficient length for introduction into the patient and for manipulation from the point of insertion to the specific desired location within the heart. Merged with the distal end of the first section of the outer guiding introducer is the second section which is comprised of a curved section, curving to the left as shown in FIG. 3A. The curve of FIG. 3A has a radius of about 1.0 to about 2.0 in. and preferably from about 1.3 to about 1.7 in. The extent of the arc of the curve is from about 135 to 225 degrees, and preferably from about 160 to about 200 degrees ending in the distal tip of the outer guiding introducer. As with the inner guiding introducer, the arc of the curve is preferably a single curve, although alternatively two or more curved sections, each with the same or different curvatures and radii which may also incorporate one or more straight sections, can be used in combination as long as the combination of separate curvatures, radii and straight sections creates the same overall curvature of the second section of about 135 to about 225 degrees and preferably from about 160 to about 200 degrees. The first and second sections are preferably coplanar (within about 15 degrees of coplanar).

The distal tip of the inner and outer guiding introducer may be, and preferably will be, tapered to form a good transition with a dilator. This tapering is preferably less than 10° and more preferably about 4° to about 7°. The inner and outer guiding introducers preferably also contain one or a multitude of radiopaque tip marker bands near the distal tip of the inner and outer guiding introducers. These inner and outer guiding introducers also preferably contain one or a plurality of vents near the distal tip of the inner and outer guiding introducers, preferably three or four such vents. The vents are preferably located no more than about 1.00 in. from the distal tip of the inner and outer guiding introducer and more preferably 0.10 to about 1.00 in. from the distal tip. The size of these vents should be in the range of about 40 to about 60/1000 of an inch in diameter. These vents are designed to prevent air from entering the guiding introducer system caused by the withdrawal of the catheter contained within the inner guiding introducer in the event the distal end of the guiding introducer system is occluded. For example, if the tip of the inner or outer guiding introducer is placed against the myocardium and the catheter located within the guiding introducer is withdrawn, a vacuum may be created within the guiding introducer system if no vents are provided. If such vacuum is formed, air may be forced back into the guiding introducer system by the reintroduction of a catheter into the lumen of the inner guiding introducer. Such air could cause significant problems in the patient, including the possibility of a stroke, heart attack or other such problems common with air embolisms. The addition of vents near the distal tip of the inner and outer guiding introducers prevents the formation of such vacuum by permitting fluid, presumably blood, to be drawn into the lumen of the inner and outer guiding introducer as the catheter is being removed from the inner guiding introducer, thus preventing the creation of a vacuum which could cause air to enter the guiding introducer system.

The inner and outer guiding introducers may be made of any material suitable for use in humans which has a memory or permits distortion from, and substantial return to, the desired three dimensional shape. For the purpose of illustration and not limitation, the internal diameter of the inner and outer guiding introducer may vary from about 6 to about 12 "French" respectively (1 French equals ⅓ of a millimeter). Such inner and outer guiding introducers can also accept dilators and appropriate guidewires. Obviously, if larger or smaller dilators or catheters are used in conjunction with the guiding introducer system of the instant invention, modifications in size or shape can be made to the inner and outer guiding introducers.

Variations in size and shape of the inner and outer guiding introducers are also intended to encompass pediatric uses, although the preferred uses are for adult human hearts. It is well recognized that pediatric uses may require reductions in size of the various sections of the inner and outer guiding introducer, in particular the first section, but without any significant modification to the shape or curve of the inner and outer guiding introducer.

In addition, variations in size or shape of the inner and outer guiding introducers are also intended to encompass the specialized situations that sometimes occur in patients with enlarged or rotated hearts.

Figure 1A:
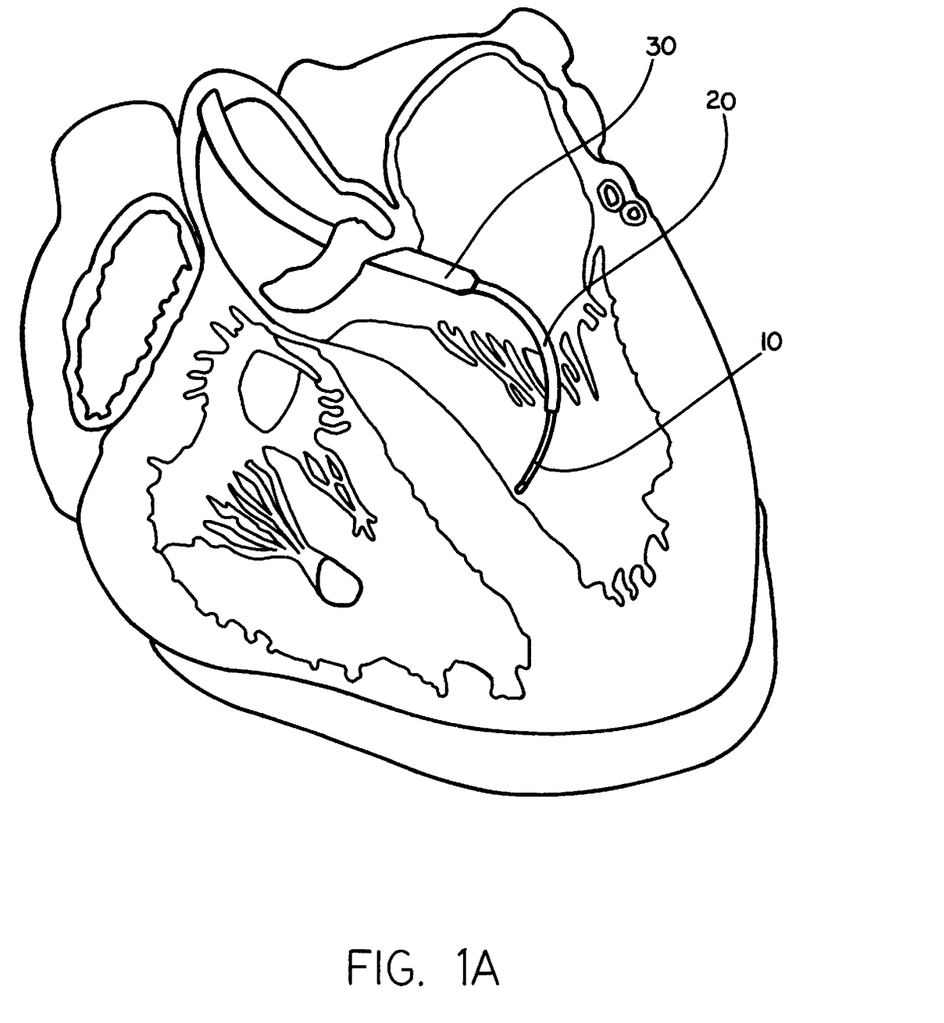
FIG. 1A is a cut away view of the heart showing the guiding introducer system supporting a catheter for ablation procedures on the left ventricular septal wall.
Figure 1B:
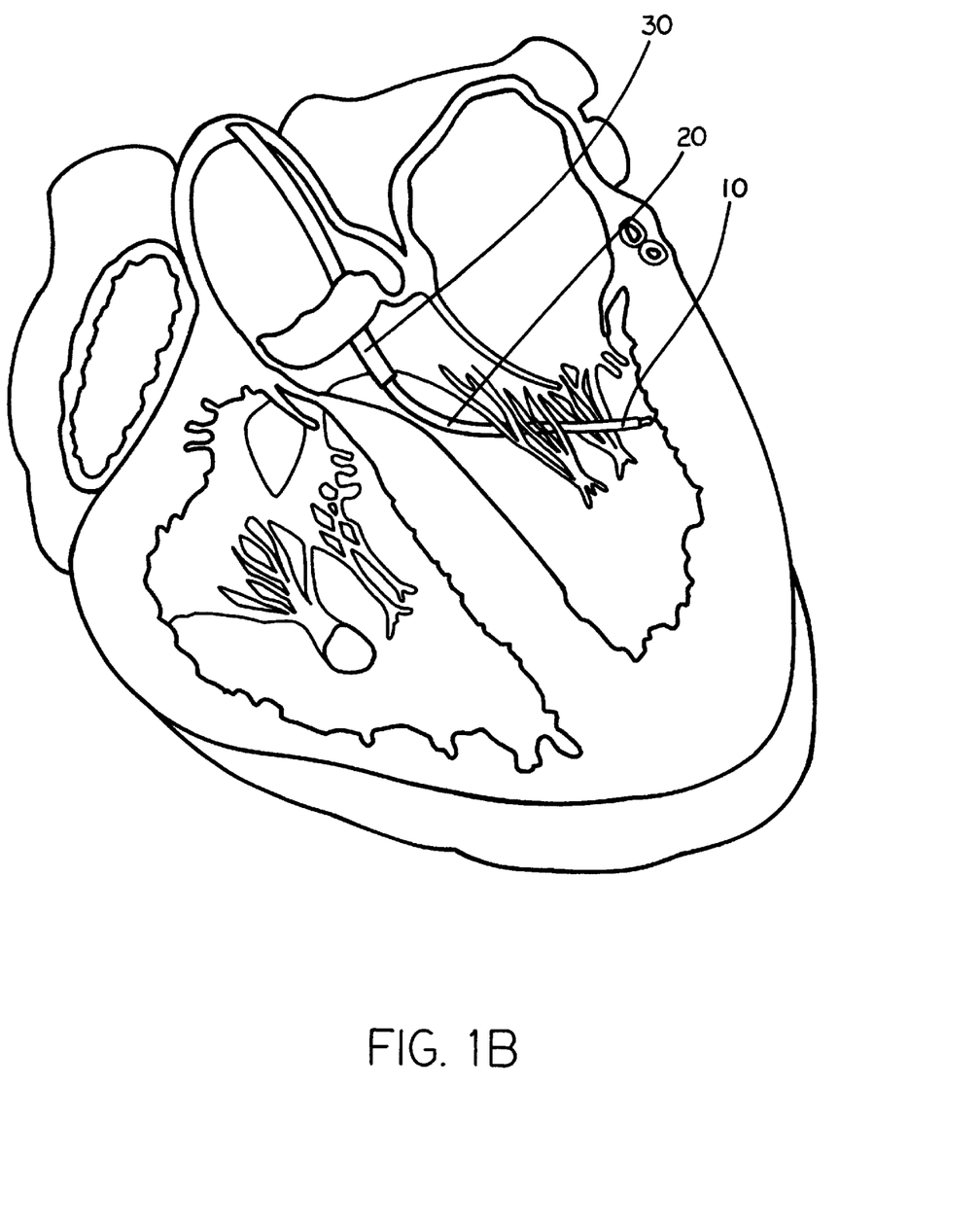
FIG. 1B is a cut away view of the heart showing the guiding introducer system for ablation procedures on the left ventricular lateral wall.

By extending the distal tip of the inner guiding introducer away from the distal tip of the outer guiding introducer and by rotating the inner guiding introducer with respect to the outer guiding introducer, a variety of shapes of the overall guiding introducer system are formed which are helpful in directing the mapping and/or ablating catheter toward the site within the left ventricle of interest. These shapes permit ablation procedures within the left ventricle to be performed, for example, located on the lateral freewall, posterior freewall, septal freewall and anterior freewall. See FIGS. 1A and 1B. The various locations can be treated by extending the inner guiding introducer away from the outer guiding introducer which forms a different overall shape and/or by rotating the inner guiding introducer with respect to the outer guiding introducer. In addition, by manipulation of the inner guiding introducer within the outer guiding introducer, additional procedures can be performed within the left ventricle. Being able to extend the inner guiding introducer within the outer guiding introducer and to rotate the inner guiding introducer within the outer guiding introducer permits a wide variety of overall shapes, which is particularly useful to medical practitioners. The medical practitioner is able to determine the relative location of the inner and outer guiding introducers because of the tip markers located near the distal tip of both the inner and outer guiding introducers.

The relative diameter of the outer guiding introducer in relation to that of the inner guiding introducer should be sufficient to permit the inner guiding introducer to be torqued or rotated within the outer guiding introducer without undue restriction on such movement. Preferably, the difference in size between the inner and outer guiding introducer should be at least about 3 French. For example, in one preferred embodiment, the outer guiding introducer is 11 French in size and the inner guiding introducer is 8 French. By this difference in diameter, there is approximately 1 French unit of space available between the outer surface of the inner guiding introducer and the inner surface of the outer guiding introducer. Preferably, this space between the inner and outer guiding introducer is filled with a biocompatible solution, such as a saline solution, preferably a heparinized saline solution. This saline solution also provides lubricity to the inner and outer guiding introducers, allowing more accurate torquing of the inner guiding introducer within the outer guiding introducer. In addition, it is preferable that the structure of both the inner and the outer guiding introducer have a high torsional constant to allow for the full utilization of the various shapes available by rotation and extension of the inner guiding introducer in relation to the outer guiding introducer. To permit this high torsional constant, in one preferred embodiment the inner guiding introducer is braided to provide further strength and structural stability.

In operation, a modified Seldinger technique is normally used for the insertion of the catheter into the femoral artery. The appropriate vessel is accessed by needle puncture. A soft flexible tip of an appropriately sized guidewire is then inserted through and a short distance beyond the needle into the vessel. Firmly holding the guidewire in place, the needle is removed. The guidewire is then advanced through the artery up to the aorta, across the aortic valve into the left ventricle. With the guidewire in place, a dilator is then placed over the guidewire with the guiding introducer system placed over the dilator. The dilator and guiding introducer system generally form an assembly to be advanced together along the guidewire into the left ventricle. After insertion of the assembly, the guidewire and dilator are then withdrawn. The catheter to be used for treatment of left ventricular tachycardia is advanced through the lumen of the inner guiding introducer and is placed at an appropriate location in the left ventricle.

By extending and withdrawing the inner guiding introducer in relation to the outer guiding introducer and by rotating the inner guiding introducer within the outer guiding introducer, variances in the overall shape and location of the guiding introducer system can be achieved.

By movement of the inner guiding introducer within the outer guiding introducer in conjunction with fluoroscopic viewing, the distal portion of the outer guiding introducer can be manipulated to direct the distal end of a catheter placed within the lumen of the inner guiding introducer to a specific internal surface within the left ventricle. In addition, by providing sufficient rigidity, the distal end of the inner guiding catheter can be maintained in that fixed location or surface position of the endocardial structure to permit the appropriate procedures to be performed. If sensing procedures are involved, the guiding introducer system is maneuvered to the desired location. At that point, the electrical activity of the heart peculiar to that location can be precisely determined by use of an electrophysiology catheter placed within the guiding introducer system. Further, as the guiding introducer system permits precise location of catheters, an ablation catheter may be placed at a precise location for destruction of the cardiac tissue by the use of energy, for example, radio frequency, thermal, laser or direct current (high energy direct, low energy direct and fulgutronization procedures). Preferably, radio frequency energy is utilized for the ablation procedure.

The precise placement of the ablation catheter electrode is important as there will be no dilution of the energy delivered due to unfocused energy being dissipated over the entire cardiac chamber and lost in the circulating blood by a constantly moving tip of the ablating catheter. This system permits a significantly reduced amount of energy to be applied while still achieving efficient ablation. Further, time used to perform the procedure is significantly reduced over procedures where no guiding introducer system is used. This reduction in time also reduces the amount of fluoroscopy that is necessary for the procedure. The precise placement of the ablation catheter within the left ventricle is particularly important because of the difficulties associated with the ablation of left ventricular tachycardia.

Ablation procedures for the treatment of tachycardia in the left ventricle may require significantly longer time because the wall of the left ventricle is significantly thicker than other tissue in the heart. It has been determined that the time of ablation must be substantially lengthened to achieve not only two dimensional ablation but also the three dimensional ablation that is necessary for the ablation of left ventricular tissue. Thus, not only is the precise location of the ablation electrode necessary, but continuous contact of the ablation electrode with the left ventricle is also necessary. Larger or longer electrodes of the ablation catheter may be necessary to achieve efficient and effective ablation. Further, other types of energy than radio frequency may be necessary for the extensive ablation necessary for the elimination of the location within the ventricle.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A guiding introducer system for use with an ablating catheter for the treatment of ventricular tachycardia in the left ventricle of the heart, comprising an inner and outer guiding introducer, wherein each contains a lumen running lengthwise therethrough, a proximal and a distal end, and wherein the outer guiding introducer is formed in a predetermined shape consistent with anatomy of the left ventricle, which shape assists in placement of the catheter in the left ventricle.

2. The guiding introducer system of claim 1 wherein the inner guiding introducer comprises a first and a second section.

3. The guiding introducer of claim 2 wherein the first section is an elongated, hollow, generally straight section of sufficient length for introduction into the patient and for manipulation from the point of insertion through to a desired location within the heart.

4. The guiding introducer system of claim 2 wherein the second section is a generally curved section with an overall radius of about 0.5 in. to about 1.5 in. and an overall arc from about 45 to about 135 degrees.

5. The guiding introducer system of claim 2 wherein the second section is a curved section with a radius of about 0.8 in. to about 1.2 in. and an arc of the curve from about 60 to about 120 degrees.

6. The process of claim 2 wherein the second section is a curved section with an overall arc, comprising one or more individual curved portions, wherein the overall arc is from about 45 to about 135 degrees.

7. The process of claim 6 wherein one or more generally straight portions are included with the one or more individual curved portions of the curved section.

8. The guiding introducer system of claim 1 wherein the outer guiding introducer is comprised of a first and second section.

9. The guiding introducer system of claim 8 wherein the first section of the guiding introducer is an elongated, hollow, generally straight section of sufficient length for introduction into the patient and for manipulation from the point of insertion through to a desired location within the heart.

10. The guiding introducer system of claim 8 wherein the second section of the outer guiding introducer is a generally curved section with an overall radius of about 1.0 in. to about 2.0 in. and an overall arc from about 135 to about 225 degrees.

11. The guiding introducer system of claim 8 wherein the second section is a curved section with a radius of about 1.3 in. to about 1.7 in. and an arc from about 160 to about 200 degrees.

12. The guiding introducer system of claim 8 wherein the second section is a curved section with an overall arc, comprising one or more individual curved portions, wherein the overall arc is from about 135 to about 225 degrees.

13. The guiding introducer system of claim 12 wherein one or more generally straight portions are included with the one or more curved portions of the curved section.

14. A guiding introducer system for use with an ablating catheter for the treatment of ventricular tachycardia in the left ventricle of the heart, comprising an inner and outer guiding introducer, wherein each contains a lumen running lengthwise therethrough, a proximal and a distal end, wherein the inner guiding introducer comprises a first and second section and wherein the second section comprises a curved section with an overall arc from about 45 degrees to about 135 degrees.

15. The guiding introducer system of claim 14 wherein the overall arc of the second section has a radius of about 0.5 in. to about 1.5 in.

16. The guiding introducer system of claim 14 wherein the overall arc of the second section is from about 60 degrees to about 120 degrees with a radius of about 0.8 in. to about 1.2 in.

17. A guiding introducer system for use with an ablating catheter for the treatment of ventricular tachycardia in the left ventricle of the heart, comprising an inner and outer guiding introducer, wherein each contains a lumen running lengthwise therethrough, a proximal and a distal end, wherein the outer guiding introducer comprises a first and second section and wherein the second section comprises a generally curved section with an overall arc from about 135 degrees to 225 degrees.

18. The guiding introducer system of claim 17 wherein the arc of the second section of the outer guiding introducer has a radius of about 1.0 in. to about 2.0 in.

19. The guiding introducer system of claim 17 wherein the arc of the second section is from about 160 degrees to about 200 degrees with a radius of about 1.3 in. to about 1.7 in.

20. The guiding introducer system of claim 17 wherein one or more generally straight portions are included with one or more curved portions of the curved section.

* * * * *